(12) United States Patent
Mueller

(10) Patent No.: US 8,129,684 B2
(45) Date of Patent: Mar. 6, 2012

(54) DETECTION OF HIDDEN OBJECTS BY TERAHERTZ HETERODYNE LASER IMAGING

(75) Inventor: Eric R. Mueller, West Suffield, CT (US)

(73) Assignee: Coherent, Inc., Santa Clara, CA (US)

( * ) Notice: Subject to any disclaimer, the term of this patent is extended or adjusted under 35 U.S.C. 154(b) by 1291 days.

(21) Appl. No.: 11/085,859

(22) Filed: Mar. 22, 2005

(65) Prior Publication Data

US 2006/0214107 A1 Sep. 28, 2006

(51) Int. Cl.
*G01J 5/02* (2006.01)
(52) U.S. Cl. .............. 250/341.8; 250/330; 250/336.1
(58) Field of Classification Search .......... 250/341.8, 250/336.1, 330
See application file for complete search history.

(56) References Cited

U.S. PATENT DOCUMENTS

| | | | |
|---|---|---|---|
| 4,084,158 A | 4/1978 | Slawsby | 342/25 F |
| 4,280,127 A | 7/1981 | Lee et al. | 342/25 A |
| 5,022,091 A | 6/1991 | Carlson | 382/240 |
| 5,227,800 A * | 7/1993 | Huguenin et al. | 342/179 |
| 5,936,237 A | 8/1999 | van der Weide | 250/234 |
| 5,969,662 A | 10/1999 | Hellsten | 342/25 A |
| 6,078,047 A * | 6/2000 | Mittleman et al. | 250/338.1 |
| 6,150,972 A | 11/2000 | Bickel et al. | 342/25 C |
| 6,341,006 B1 * | 1/2002 | Murayama et al. | 355/53 |
| 6,395,555 B1 * | 5/2002 | Wilson et al. | 436/68 |
| 6,525,862 B2 | 2/2003 | Fisher et al. | 359/278 |
| 7,087,902 B2 | 8/2006 | Wang et al. | 250/341.1 |
| 2003/0178584 A1 | 9/2003 | Arnone et al. | 250/495.1 |
| 2004/0061055 A1 | 4/2004 | Kawase et al. | 250/330 |
| 2004/0065831 A1 * | 4/2004 | Federici et al. | 250/341.1 |
| 2004/0140924 A1 | 7/2004 | Keller et al. | 342/22 |
| 2004/0155665 A1 | 8/2004 | Arnone et al. | 324/644 |
| 2004/0252024 A1 | 12/2004 | Huey et al. | 340/540 |
| 2004/0263379 A1 | 12/2004 | Keller | 342/22 |
| 2005/0230604 A1 | 10/2005 | Rowe et al. | 250/221 |
| 2005/0231415 A1 | 10/2005 | Fleisher et al. | 342/22 |
| 2005/0231421 A1 | 10/2005 | Fleisher et al. | 342/179 |
| 2005/0232459 A1 | 10/2005 | Rowe et al. | 382/100 |
| 2005/0242287 A1 | 11/2005 | Hakimi | 250/363.09 |
| 2006/0016997 A1 * | 1/2006 | Siegel et al. | 250/339.11 |

(Continued)

FOREIGN PATENT DOCUMENTS

GB 2359716 A * 8/2001

OTHER PUBLICATIONS

Müller et al., Electrically tunable, room-temperature quantum-cascade lasers, Applied Physics Letters, vol. 75, No. 11 (Sep. 1999), pp. 1509-1511.*

(Continued)

*Primary Examiner* — David Porta
*Assistant Examiner* — Shun Lee
(74) *Attorney, Agent, or Firm* — Morrison & Foerster LLP

(57) ABSTRACT

A THz-frequency heterodyne imaging method is used to remotely detect objects concealed in or under a person's clothing. One THz-frequency beam is scanned over a person being examined. A portion of the beam penetrates the persons clothing and is reflected by an object concealed under the person's clothing. The reflected portion the beam is mixed with another beam of THz-frequency radiation having a different frequency to provide a signal having an intermediate frequency (IF) including image data representative of the concealed object.

5 Claims, 2 Drawing Sheets

U.S. PATENT DOCUMENTS

| | | | |
|---|---|---|---|
| 2006/0022140 A1 | 2/2006 | Connelly et al. | 250/338.1 |
| 2006/0055936 A1 | 3/2006 | Yun et al. | 356/479 |
| 2006/0056586 A1 | 3/2006 | Uetake et al. | 378/57 |
| 2006/0104480 A1 | 5/2006 | Fleisher | 382/103 |
| 2006/0164287 A1 | 7/2006 | Holt et al. | 342/22 |
| 2006/0214107 A1 | 9/2006 | Mueller | 250/341.8 |
| 2006/0235621 A1 | 10/2006 | Cole et al. | 702/19 |
| 2006/0239404 A1 | 10/2006 | Udpa et al. | 378/62 |

OTHER PUBLICATIONS

E.R. Mueller, "Frequency-Shifting Submillimeter Single-Sideband Receiver," *International Journal of Infrared and Millimeter Waves*, vol. 15, No. 4, 1994, pp. 665-670.

In re U.S. Appl. No. 11/231,079, filed Sep. 20, 2005, by Eric Mueller, entitled "Identification of Hidden Objects by Terahertz Heterodyne Laser Imaging".

S. Wang et al., "Pulsed terahertz tomography," *Journal of Physics D: Applied Physics*, vol. 37, No. 4, Feb. 21, 2004, pp. R1-R36.

X.-C. Zhang, "Three-dimensional terahertz wave imaging," *Phil. Trans. R. Soc. Lond. A*, vol. 362 (2004), pp. 283-299.

F. Oliveira et al., "Analysis of Terahertz Spectral Images of Explosives and Bio-Agents Using Trained Neural Networks," *Proc. SPIE*, vol. 5411 (2004), pp. 1-6.

Article, "Terahertz Scattering for Detection of Improvised Explosive and Bio-agent Dispersal Devices," *NEAR-LAB (Northwest Electromagnetic and Acoustics Research Laboratory*, printed Sep. 19, 2005, from http://nearlab.ece.pdx.edu/terahertz_imaging.htm web site, 3 pages. in length.

S. Wang et al., "Tomographic imaging with a terahertz binary lens," *Applied Physics Letters*, vol. 82, No. 12, Mar. 24, 2003, pp. 1821-1823.

D.J. Cook et al., "Quantitative THz Spectroscopy of Explosive Materials," *Optical Society of America (PSI-SR-1196)*, Mar. 14-16, 2005, 4 pages in length.

Powerpoint presentation by J.F. Federici et al., "Terahertz Imaging and Detection of Suicide Bombers," *NJIT Department of Physics*, Funded by US Army and NSF (Jan. 2005),16 pages in length.

M. Coulombe et al., "Submillimeter-Wave Polarimetric Compact Ranges for Scale-Model Radar Measurements," *IEEE MTT-S International*, vol. 3 (2002), pp. 1583-1586.

G.B. DeMartinis et al., "A 1.56 THz Spot Scanning Radar Range for Fully Polarimetric W-Band Scale Model Measurements," *Antenna Measurements Techniques Association*, Oct. 2000, 6 pages in length.

J.C. Dickinson et al., "High Resolution Imaging using 32 GHz and 1.5 THz Transceivers," *15th International Symposium on Space Terahertz Technology*, Apr. 27-29, 2004, 8 pages in length.

T.M. Goyette et al., "A 1.56 THz compact radar range for W-band imagery of scale-model tactical targets," *Proc. SPIE*, vol. 4053, Aug. 2000, pp. 615-622.

E.R. Mueller et al., "Power and Spatial Mode Measurements of Sideband Generated, Spatially Filtered, Submillimeter Radiation," *IEEE Transactions*, vol. 42, Issue 10, Oct. 1994, pp. 1891-1895.

\* cited by examiner

DETECTION OF HIDDEN OBJECTS BY TERAHERTZ HETERODYNE LASER IMAGING

TECHNICAL FIELD OF THE INVENTION

The present invention relates in general to terahertz (THz) lasers. The invention relates in particular to imaging using THz-laser radiation reflected or backscattered from a target by heterodyning the reflected radiation with a signal from another terahertz laser and processing the difference signal to provide an image.

DISCUSSION OF BACKGROUND ART

The terahertz frequency spectral range is a relatively underdeveloped band of the electromagnetic spectrum. The terahertz band is bordered by the infrared on the short-wavelength side and millimeter-waves on the long-wave length side. The terahertz band encompasses radiation having a frequency range of 0.3 to 10 THz and wavelengths between about 30 micrometers (μm) and 1 millimeter (mm). The terahertz band is sometimes referred to by practitioners of the art as the far infrared (FIR).

Many materials that are opaque to wavelengths shorter then 30 micrometers are either transparent or semi-transparent in the terahertz band. Such materials include plastic, textiles, paper, cardboard, wood, ceramics, opaque glasses, semiconductors, and the like. Radiation at longer wavelengths, for example, millimeter waves have better transmissivity than terahertz radiation in these materials but the longer wavelengths are unsuitable for use in high resolution imaging systems. Further, such materials do not have much spectral content, i.e., characteristic absorption lines, in these longer wavelength regions that would allow one to be easily distinguished from another.

Terahertz radiation is not an ionizing radiation, so it does not have the potential to present health problems as would, for example, X-radiation (X-Rays). Terahertz radiation can be propagated for much longer distances in the atmosphere than X-rays, for example, several meters, and does not cause damage to electronic devices and unexposed film. In addition to offering a higher potential resolution in imaging than millimeter waves, terahertz radiation also offers a potential to provide sharper differentiation between different materials superimposed on one another and, accordingly provide higher contrast images than would be possible with millimeter waves.

It would be advantageous to exploit the imaging potential of terahertz radiation in security apparatus for examining persons, luggage or packages for concealed objects or substances. Such objects and substances could include explosives, guns, knifes, drugs, biological agents, and the like. Theses objects or substances could be concealed under a person's clothing, or in non-metallic containers or luggage to be transported in airplanes, trains, buses, ships.

SUMMARY OF THE INVENTION

The present invention is directed to remotely detecting objects or substances concealed in or under a person's clothing. In one aspect a method of detecting the concealed objects comprises scanning a first beam of THz-frequency radiation, from a first source thereof over the person. A portion of said first beam penetrates the person's clothing and is reflected from an object or substance concealed under the person's clothing. The reflected portion of said first beam is mixed with THz-frequency radiation from a second source thereof to provide a signal having an intermediate frequency (IF) and including image data representative of the concealed object or substance.

The first beam can be scanned in a predetermined pattern over the person. The image data from the IF signal can be processed together with data representative of the scanning pattern to provide a displayable image. The THz-frequency radiation of the signal-frequency beam can at least partially penetrate fabrics commonly used for clothing. Accordingly, radiation reflected from the person will include information on any objects or substances in or under that clothing and those objects or substances will be visible in the displayed image.

In a preferred embodiment of the inventive method the THz-frequency radiation from the second source has an essentially fixed frequency, and the THz-frequency radiation from said first source is periodically varied during the scanning. The first beam of THz-frequency radiation is scanned over a region to be imaged, including the person, in a scan period, and the variation period of the first-source THz-frequency is equal or less than the scan period divided by a number equal to the number of image elements in the displayable image.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the present invention.

DETAILED DESCRIPTION OF THE INVENTION

Figure 1:
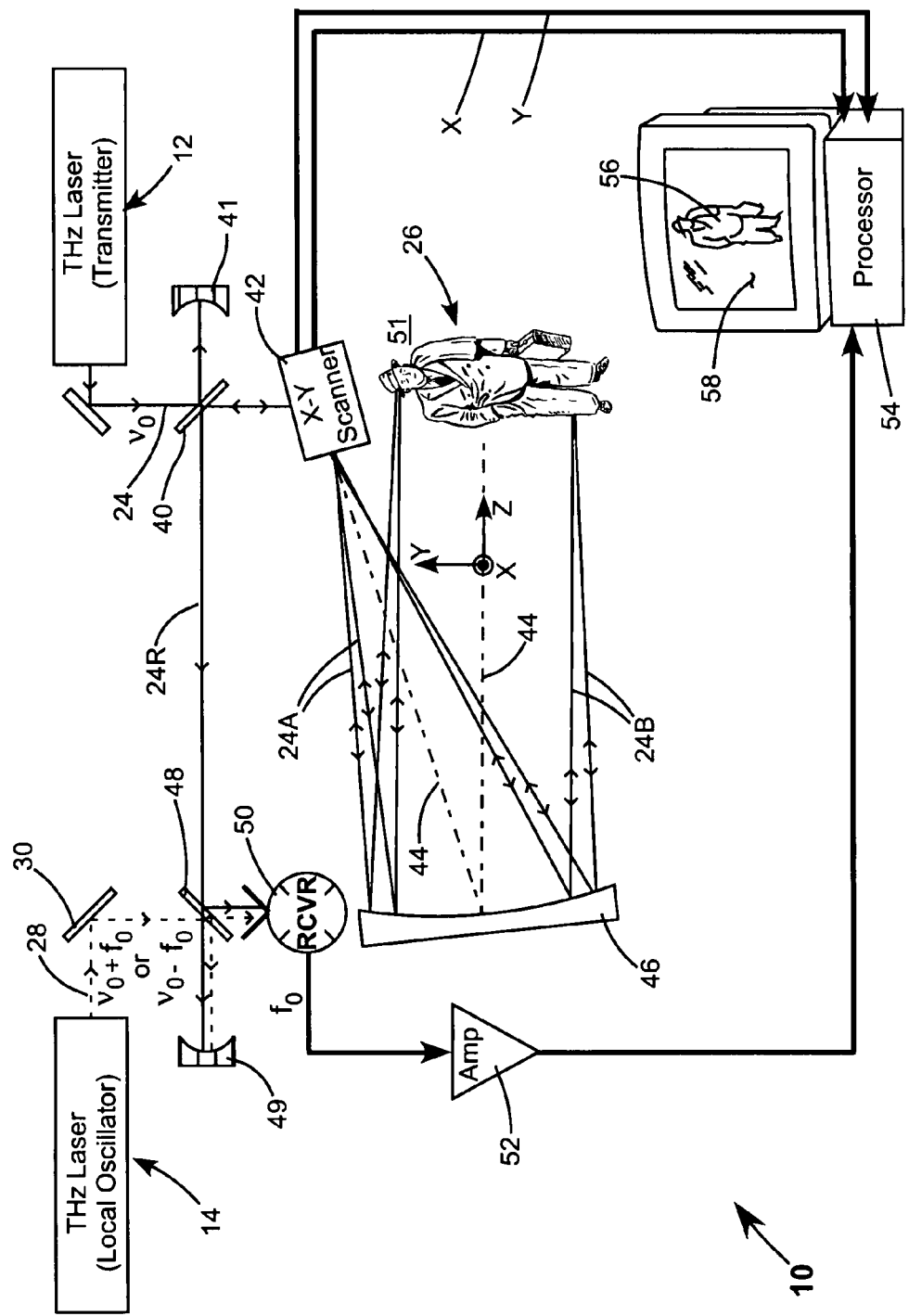
FIG. 1 schematically illustrates one preferred embodiment of a apparatus in accordance with the present invention for remotely detecting objects concealed under a persons clothing, the apparatus including a THz laser generating radiation at a signal frequency, an optical arrangement for scanning the signal-frequency radiation over a person, receiving reflected signal-frequency radiation from the person, and directing the reflected signal-frequency radiation to a receiving detector in which the reflected signal-frequency radiation is heterodyned with radiation from another THz-laser functioning as a local oscillator and having a different frequency, the mixing providing an intermediate-frequency (IF) signal including image information, the IF signal being processed together with scanning information to provide an image of the person.

Referring now to the drawings, wherein like components are designated by like reference numerals, FIG. 1 schematically illustrates one preferred embodiment 10 of scanning THz imaging apparatus in accordance with the present invention. In FIG. 1, and in other drawings referred to herein below, the path of optical (THz) radiation is depicted by single-weight lines, either solid or dashed depending on frequency. The direction of propagation of the radiation is indicated by open arrowheads. Electronic connections are depicted by double-weight solid lines with the direction of electronic communication indicated, where appropriate, with a solid arrowhead.

Apparatus 10 includes two sources 12 and 14 of THz radiation. Here each of the sources is a THz-laser. A preferred THz laser for the inventive method is an optically pumped THz-laser in which a gaseous gain-medium is pumped by radiation from a $CO_2$ laser. A THz-laser may have different nominal frequencies depending on the gaseous THz gain-medium. Any particular gain-medium has different discrete lasing frequencies about some nominal frequency characteristic of that gain-medium. Accordingly, it is possible to select an output frequency $v_0$ from many different THz frequencies between about 0.3 THz and 5.0 THz, by selecting a particular gain-medium and adjusting a diffraction grating within the THz resonator. Such $CO_2$ laser-pumped THz-lasers are commercially available. One such commercially-available THz-laser is a SIFIR-50 THz-laser available from Coherent Inc. of Santa Clara, Calif. This laser has excellent spatial mode quality and can emit between about 50 milliwatts (mW) and 100 mW of continuous wave (CW) power.

$CO_2$ laser-pumped THz lasers are preferred for apparatus 10 because of advantages including a wide range of available THz frequencies, relatively high power output, and reliability. Those skilled in the art, however, will appreciate that in theory at least, other THz radiation sources both laser and electronic may be used without departing from the spirit and scope of the present invention. By way of example, one possible electronic source of THz radiation is backward-wave oscillator. Such an oscillator can emit up to 1.0 mW of CW power at (discrete) frequencies up to about 1.5 THz. THz backward-wave oscillators are at a less mature stage of development than THz-lasers and may not be as reliable as commercially available THz-lasers.

Other possible THz-lasers include Quantum cascade semiconductor lasers (QCL). These have an advantage of being relatively small by comparison with $CO_2$ laser-pumped THz lasers. Another advantage is that continuous tuning is possible over frequencies up to about 6 THz. QCL lasers, however, must be operated at liquid Helium temperatures in order to achieve milliwatts of power output. In room temperature operation, output power is presently limited to only a few nanowatts (nW).

Another possible THz source is laser-triggered gallium arsenide (GaAs) photomixer. Such a source can provide radiation over the entire THz range but with output power limited to tens of nanowatts. In addition to providing only limited output power, GaAs photomixer sources are pulsed rather than CW sources. CW THz sources are preferred in embodiments of the present invention. In addition, it is preferred that these sources be essentially narrowband (including tunable narrowband) devices. This can be contrasted with short pulse sources that are selected for their broadband characteristics.

Continuing with reference to FIG. 1, in apparatus 10, THz-radiation source 12 provides a beam 24 of radiation (the signal beam), having a frequency $v_0$, which will be used to scan a person 26 for providing an image of that person. Apparatus 10 is a heterodyne imaging system for which THz-radiation source 14 functions as a local oscillator (LO). A beam 28 of radiation from THz-radiation source 14 is required to have a frequency that is offset from the frequency $v_0$ of the signal beam 24 by a frequency $f_0$. Frequency $f_0$ is one preferred frequency of an electronic signal including image data that will be electronically processed to provide an image of the person being scanned.

For a frequency offset $f_0$ between about 0.5 MHz and 15.0 MHz lasers 12 and 14 preferably have the same gain medium with laser 12 having an output frequency $v_0$ near the peak of the gain curve and laser 14 electronically tuned to output radiation at a frequency $v_0+f_0$ or $v_0-f_0$ where these frequencies are frequencies of transitions of the gain medium adjacent the transition of peak gain. This frequency offsetting method for gas lasers, and circuits therefor, are well known in the art and a detailed description thereof is not necessary for understanding principles of the present invention. A detailed description is included in U.S. patent application Ser. No. 10/760,687, filed Jan. 20, 2004, assigned to the assignee of the present invention, and the complete disclosure of which is hereby incorporated by reference.

The gain-medium of a THz laser typically consists of large, heavy gas molecules, for example, methanol ($CH_3OH$) or difluoromethane ($CH_2F_2$). Because of this, there are many possible laser transitions for any gas, spectrally very closely spaced. Accordingly, values for $f_0$ using this frequency offsetting method are typically in the above referenced MHz range. For values of $f_0$ between about 500 MHz and 200 GHz, lasers 12 and 14 preferably have different gain-media.

Continuing with reference to FIG. 1, beam 24 is incident on a beamsplitter 40. A portion of the beam is transmitted through beamsplitter 40 to a scanner 42. Scanner 42 scans the beam in a raster fashion in X and Y-axes perpendicular to each other and perpendicular to the general direction of propagation of the beam or system axis, indicated in FIG. 1 by alternately short and long-dashed line 44. As two-axis beam scanners are well-known in the art, a detailed description of the scanner is not presented herein. A preferred splitting ratio for beamsplitter 40 is 50:50. The reflected portion of beam 24 is directed to a beam dump 41.

Beam 24 (the signal beam) expands out of the scanner and is incident on a mirror 46 at a position thereon dependent on the instant scan direction. Beam 24, here, is depicted in extreme positions in the Y-axis scan-direction by ray pairs 24A and 24B. Mirror 46 can be described as an antenna of the apparatus and refocuses the scanned beam in a region 51 in which persons to be scanned will be located. Radiation reflected from the person being scanned returns along the incident path and is refocused back into scanner 42 by mirror 46. The reflected beam is collimated in the scanner and directed out of the scanner to beamsplitter 40. A portion of the reflected beam is directed toward another beamsplitter 48 along a path 24R.

A portion of the reflected signal beam 24R is reflected by beamsplitter 48 onto a detector 50. Detector 50 is preferably a corner-cube mounted Schottky-diode detector, as schematically depicted in FIG. 1, and can be described as a receiver (RECR) of the apparatus. Such detectors are commercially available, for example, from Virginia Diode Inc. of Charlottesville, Va.

Most, for example about 95%, of beam 28 from THz source 14 is reflected by beamsplitter 30 to beamsplitter 48. Beamsplitter 48 transmits a portion of beam 28, and that transmitted portion of beam 28 is also incident on detector 50. A Reflected portion of beam 28 and a transmitted portion of beam 24R is directed to a beam dump 49.

Preferably beamsplitter 48 has a reflectivity higher than 50% to maximize the portion of reflected beam 28 that is incident on detector 50. For a given power in beam 28, the transmission of beamsplitter 48 for radiation having frequency $v_0 \pm f_o$ is selected to allow sufficient power to be incident on detector 50 to "swamp" out other noise sources of the detector.

The wave fronts of the portions of beams 24R and 28 incident on the detector are preferably aligned to be parallel. The diameter of the two beam portions are also preferably arranged to be equal. The beam portions, one having a frequencies $v_0 \pm f_o$ and the other having a frequency $v_0$ interfere on the surface of the detector to provide a signal from the detector having the offset frequency $f_o$. The signal varies in amplitude according to the instant intensity of reflected beam 24R, which, in turn, is dependent on the reflection from the person at corresponding instant X and Y coordinates of beam 24 on the person. The X and Y coordinates are a function of time.

The detector signal is amplified by an operational amplifier 52. The amplified signal is supplied to a processor 54. Signals from scanner 42 representative of the instant X and Y positions of the scanner are also transmitted to the processor. Accordingly, the processor is able to create a sequence of two-dimensional matrices of amplitude values (image "frames") that are used to display an image 56 of person 26 on a display device 58.

Before describing any further preferred embodiment of the present invention, it is useful to evaluate factors and parameters affecting the effectiveness of person scanning apparatus in accordance with the present invention. Such a discussion is set forth below beginning with a discussion of the effect of atmospheric loss in THz radiation propagation.

Much of the atmospheric loss in THz radiation propagation is due to absorption by water vapor. By way of example, at a frequency 2.5 THz, atmospheric loss is about 0.5 dB/m at standard temperature and pressure (STP) and 50% relatively humidity (RH). This, incidentally, is a relatively low loss compared with the loss for other frequencies in the THz range, and the 2.5 Thz frequency is readily available from a THz-laser such as a $CH_3OH$ laser. Given a round trip distance from antenna 46 to person 26 being scanned (hereinafter alternatively referred to as "the target") of about 100 meters (m) the atmospheric loss would be about 50 decibels (dB). The significance of the antenna-to-target distance is discussed further hereinbelow A preferred scan area, sufficient to include an "average" adult person, is 1.8 m×0.6 m. Preferably this area should be scanned in 1 second or less. A preferred horizontal and vertical cross-range (X and Y) resolution is 3 centimeters (cm) or less. In this case, the scan area must be divided into 1200 cross-range "cells".

It is believed, based on experimental observations, that in order to most effectively detect objects concealed under clothing, range information, in addition to amplitude information, will be required to separate the reflections of a THz signal beam from a layer or layers of clothing from reflections of objects under the clothing. Such range information would not be provided by the apparatus of FIG. 1 as depicted and described. A preferred implementation of the inventive THZ imaging method that can be used to provide such range information involves a FMCW (frequency modulated continuous wave) technique analogous to high range resolution (HRR) radar. A description of a preferred apparatus for implementing this technique is presented further hereinbelow In the inventive THz FMCW technique the signal beam, i.e., an equivalent of beam 24 of FIG. 1, is frequency modulated with a chirp or frequency sweep. If the number of scattering sites in a given X-Y scan cell is assumed to be arbitrary, the required amount of FM on the signal beam can be calculated from an equation:

$$\Delta z = c/2 * \Delta v \quad (1)$$

where $\Delta z$ is the range resolution (resolution along the Z-axis), c is the speed of light, and $\Delta v$ is the total extent of the frequency sweep (chirp) of the FM imparted to the signal beam. Accordingly, for a range resolution of 5.0 mm $\Delta v$ would need to be about 30 gigahertz (GHz) and it would be necessary that a THz-source providing the signal beam be tuneable over this 30 GHz range.

This amount of tuning can be added to a CO2 laser-pumped THz-laser, or any other optically pumped THz-laser, via an external sideband generator, and is a presently preferred method of providing tunable THz-source for use in embodiments of the present invention. Above-discussed QCL THz-sources are presently tunable only over about 6 GHz and have limited output power.

From the exemplary parameters derived above, it is possible to calculate a maximum pre-detection bandwidth in the inventive person-scanning apparatus that would be allowed to obtain a signal-to-noise ratio (SNR) of 1.0 for a scattering site that reflects all of the signal-beam back. That minimum bandwidth, combined with the available signal-beam-source power and NEP (noise equivalent power) of a receiver, can be used to calculate a minimum detectable amount of reflection or scatter from a hidden object.

Assuming the 1 s time to scan all of the 1200 AS-EL cells, and using a "$5\tau$ rule" to determine a time constant time, the minimum (post-processing) pre-detection bandwidth is 6 kilohertz KHz. For a coherent receiver, such as the preferred Schottky diode of receiver 50 of FIG. 1, this causes an increase in system NEP (when compared with a 1 second NEP standard) of 38 dB. This can be defined as $NEP_{SYS}$ which is the increase due to noise bandwidth.

Signal beam power from an SBG tuned THz-source will be almost three orders of magnitude less than would available directly from a $CO_2$ laser-pumped THz-laser. While such a laser can deliver up to one Watt of power, much of this will be lost in a sideband generator (SBG) used to tune the laser output. At present, the best reported conversion loss for a THz SBG is about 14 dB. Typical results, however, may be 10 dB worse. A THz SBG is based on a Schottky diode-element and the present maximum power handling for such a Schottky element is about 25 mW. Assuming the best result, a tunable THz-source provided by a THz-laser output frequency modulated by a Schottky diode SBG would have an output power of only about 1 mW. This is still, however, greater than would be available from a QCL having a lesser tuning range. Schottky-diode receivers operating at 2.5 THz that are presently used in satellite-borne THz atmospheric sounding systems have NEP's of about $2.8 \times 10^{-19}$ W/Hz.

Given the above assumed and calculated values, the SNR for a 100% return (reflection) from a target can be calculated for an FMCW apparatus in accordance with the present invention. The SNR can be defined by an equation:

$$SNR = (P_T/NEP) * (1/BW) * T_A \quad (2)$$

where $P_T$ is the transmitter (signal beam) power, BW is the effective pre-detection bandwidth, and $T_A$ is the transmission of the atmosphere. Accordingly, in the instant example a SNR of about 68 dB can be expected.

In the inventive FMCW technique it is important the frequency of the signal beam be swept or "chirped" through the entire tuning range in irradiating every AS-EL (X-Y) cell. Accordingly, for a 1200-cell scan in 1 second, an FM chirp generator (frequency synthesizer) is required that can perform the chirp in about 833 microseconds or less. This is possible, for example, with a COMSTRON FS5000 series direct synthesizer frequency synthesizer available from Aeroflex Corporation, of Plainview, N.J.

The minimum antenna (focusing mirror 46) size which can support the above-exemplified system can be estimated by calculating the Gaussian beam back-propagation from the target to the antenna, with the beam size at the target taken to be equal to the X-Y cell size. Assuming a factor of 3 as a rule-of-thumb for the minimum aperture that will not cause an unacceptable level of vignetting, then the antenna (mirror) size would be about 595 mm for a target range of about 50 meters. The mirror size would be about 417 mm for a target range of 35 meters, and about 299 mm target range of 25 meters.

Next, scattering loss and optical geometric loss factors for THz light scattered off of an object at a range R are considered. This object is assumed to be unresolved in X-Y, i.e., assumed to be equal to or larger in size than the signal beam. Additionally, assuming that multi-bounce events are not collected, an optimal condition is one in which the signal beam and the receiver FOV at the target are equal, i.e., the apparatus behaves as a symmetric transceiver. In this case, the scattering object can be modeled as a diffuse collection of point scatterers (small spheres), and a optical/scattering loss factor ($L_O$) can be defined by an equation:

$$L_O = A_R * r_{avg} / 2\pi R^2 \quad (3)$$

where R is the range to the target, $A_R$ is the area of the antenna, and $r_{avg}$ is the average surface reflectivity of the target at each X-Y cell. In the present example, assuming $r_{avg}$ is equal to 1.0 (100% return), and all with other parameters as presented above, then $L_O$ will be equal to $17.6 \times 10^{-6}$, i.e., −47.5 dB.

Given the above-assumed and calculated values and parameters, the SNR for an antenna-to-target range R of 50 meters will be about 21 dB, and for antenna-to-target ranges of 35 meters and 25 meters, SNRs will be 33.6 dB and 51.5 dB respectively. Any additional losses as a result of radiation passing through clothing twice or as a result of an object having a reflectivity less than 1.0 (100%) will degrade these ratios. By way of example, typical clothing might be expected to have one-way loss on the order of 4 dB at 2.5 THz. The typical THz reflectivity of metals is very nearly equal to 1.0. However, as most plastics have a refractive index around about 1.5, THz reflectivity from plastics objects may be only about 4% (−14 dB). These values for clothing losses and reflectivity would modify the above calculated SNR ratios as a function of range as follows.

At a range of 50 meters, the SNR for metal under clothing would be about 13 dB, but for plastic under clothing would be −1 dB which would be unacceptable. At a range of 25 meters, however, the SNR for metal under clothing would be about 43.5 dB, and for plastic under clothing would be about 29.5 dB.

Figure 2:
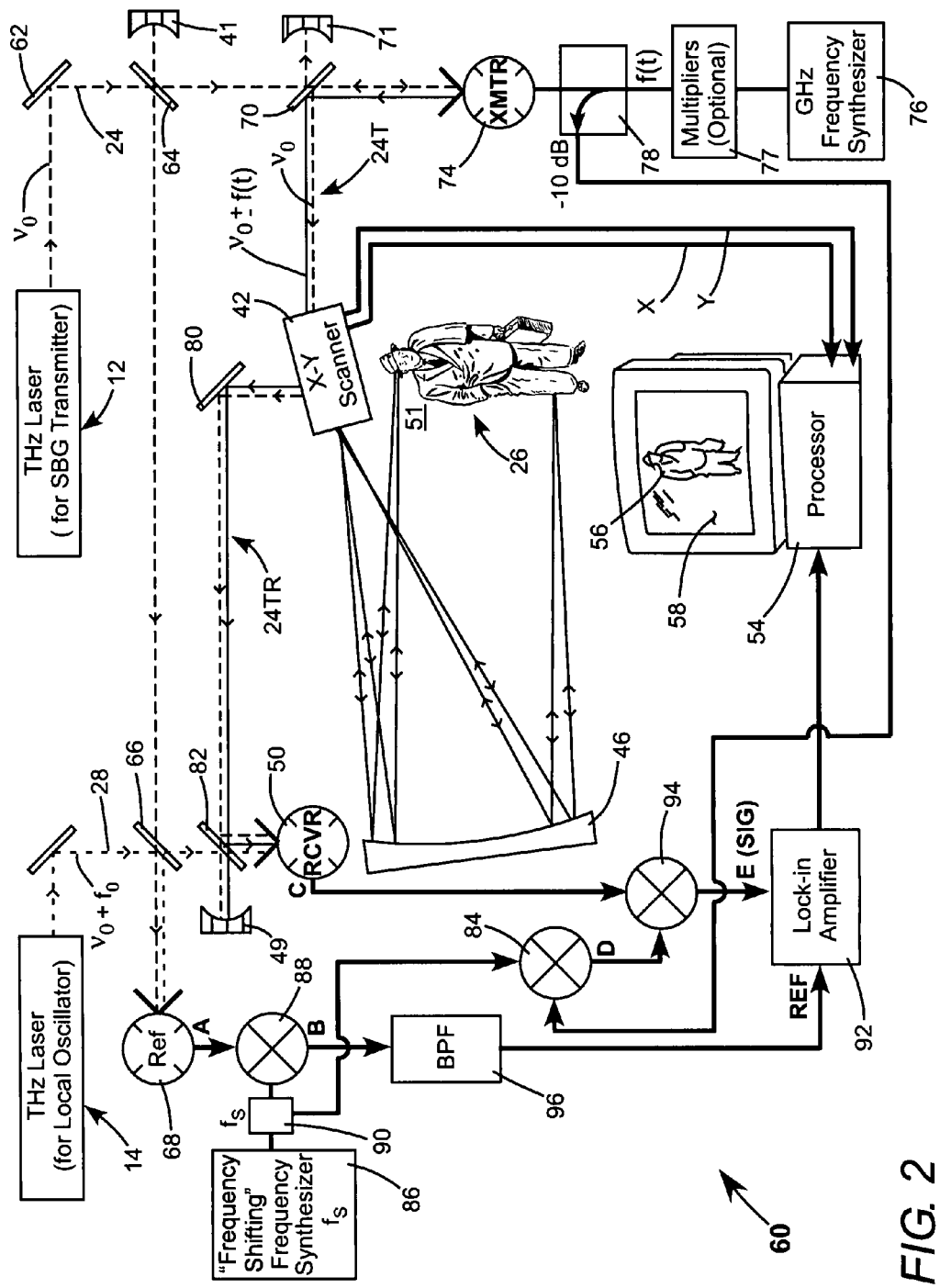
FIG. 2 schematically illustrates another preferred embodiment of a apparatus in accordance with the present invention for remotely detecting objects concealed under a persons clothing, similar to the apparatus of FIG. 1, but wherein the signal-frequency THz radiation is periodically tuned over a predetermined frequency range during scanning and the receiving detector is arranged with other components as a single sideband receiver.

Turning again to the drawings, FIG. 2 schematically illustrates another preferred embodiment 60 of scanning THz imaging apparatus in accordance with the present invention. In apparatus 60, the above-discussed FMCW technique using a tunable THz radiation source is implemented. THz radiation sources (THz-lasers) 12 and 14 are represented in simplified form, having been described in detail above. THz-laser 12 has an output frequency $v_0$, and THz-laser 14 is tuned to an output frequency of $v_0 + f_0$.

Radiation for THz-laser 12 is directed by a turning mirror 62 to a beamsplitter 64 that transmits most, for example about 95%, of the radiation and reflects the remainder (less any beamsplitter losses). The reflected portion is directed via a beamsplitter 66 to a mixer 68, preferably a corner-cube mounted Schottky diode. The function of mixer 68 is described further hereinbelow. The portion of beam 24 transmitted by beamsplitter 64 is incident on a beamsplitter 70 preferably having a transmission-to-reflection ratio of about 50:50. Unusable reflected radiation is directed to a beam dump 71.

The transmitted portion of beam 24 from beamsplitter 70 is collected by a sideband generator (XMTR) 74, again, preferably formed from a corner-cube mounted Schottky diode. This sideband generator is used to "tune" the output radiation supplied by THz-laser 12. XMTR 74 is powered by a frequency synthesizer 76 via optional frequency multipliers 77, and a directional coupler 78. THz-laser 12, XMTR 74, and frequency synthesizer 76 can be collectively considered as a tunable THz radiation source.

Frequency synthesizer 76 can generate a range of GHz frequencies from some minimum value up to some maximum value. By way of example commercial synthesizers (such as the above-referenced COMSTRON synthesizer) are available than can generate frequencies in various GHz frequency ranges. The tuning frequency range can be extended by frequency multipliers to provide at least the preferred 30 GHz range discussed above for providing a 5 mm range-resolution.

As a result of irradiation by laser radiation having frequency $v_0$ and the application of the output of the frequency synthesizer, XMTR 74 emits radiation at the original frequency and radiation at upper and lower sideband frequencies $v_0 \pm f(t)$, where f(t) represents a "tuning" frequency that is a function of time. The tuning is chirped between the maximum and minimum values, with the chirp time being determined by the time required for a complete scan divided by the number of resolution (X-Y) cells in the scan, as discussed above. XMTR 74 provides the tunable "transmitter" of apparatus 60. The frequencies emitted by XMTR 74 are reflected by beamsplitter 70 into X-Y scanner 42. Here it should be noted that beamsplitter 70 may be a silicon etalon (diplexer) arranged to transmit frequency $v_0$ and reflect frequencies $v_0 \pm f(t)$.

The scanning (transmitted) beam is designated by the general reference numeral 24T, the original and sideband frequencies are designated separately for purposes of description (by long-dashed and solid lines respectively) although, in practice, all frequencies would follow the same path. Scanner 42 cooperates with turning and focusing mirror 46 to scan a person, as described above with reference to apparatus 10 of FIG. 1. Frequencies are not separately designated in beams leaving and returning to the scanner for simplicity of illustration. Radiation reflected from person 26 (the target) leaves the scanner as a beam designated by the general reference numeral 24TR (the signal beam), again with frequencies $v_0$, and $v_0 \pm f(t)$ separately designated.

Signal beam 24TR is directed by a turning mirror 80 to a beamsplitter 82. A portion of beam 24TR is reflected by the beamsplitter into a receiver (RECR) 50, preferably a corner-cube mounted Schottky diode as discussed above with reference to apparatus 10 of FIG. 1. Beamsplitter 82 may also be a silicon etalon arranged to transmit frequency $v_0$ and reflect frequencies $v_0 \pm f(t)$ as discussed above. A portion of beam 28 from THz-laser 12 is transmitted by beamsplitter 82 and is incident on detector or receiver (RCVR) 50. Receiver 50 is also preferably a corner-cube mounted Schottky diode. Portions of beam 24TR transmitted by beamsplitter 82 and a portion of beam 28 reflected by beamsplitter 82 are trapped by a beam dump 49.

In apparatus 60 of FIG. 2, processing of signals generated by receiver 50 is more complex than in apparatus 10 of FIG. 1. This is because receiver 50 in apparatus 60 receives a greater frequency spectrum of radiations, resulting from the chirped frequency modulation of radiation from SBG (transmitter) 74. In apparatus 60, electronic processing circuitry is arranged cooperative with detector 50 to provide a single sideband (SSB) receiver. This circuitry is depicted in block form and grouped to the left of the drawing. The electronic processing circuitry is arranged to respond to only one of the sidebands f(t) in beam 24TR. A description of the operation of the single sideband receiver is set forth below with reference to the frequency content (spectrum) at various components of the electronic circuitry that are involved in a single sideband selection process. It should be noted that in describing this frequency content at these components, frequency mixing products of frequency $v_0$ or greater are ignored, as these frequencies, being in the THz frequency range, will be rapidly attenuated in coaxial cables or waveguides used for component interconnections.

Two additional signal inputs are required by the electronic circuitry to process the signals received by receiver 50. A first of these is a reference signal A. This signal is generated by above-referenced mixer 68 from the portion of beam 24 (frequency $v_0$) delivered thereto. This is mixed with a portion of beam 28 (frequency $v_0+f_0$) directed to mixer 68 by beamsplitter 66. The second additional signal input is a sample of the output of frequency synthesizer 76. This is delivered from directional coupler 78 to a mixer 84, the function of which is described further hereinbelow. In addition to these externally provided signal inputs, the electronic circuitry makes use of an internally generated signal ($f_S$) provided by a frequency synthesizer 86, the function of which is described further hereinbelow, and which can be termed a "frequency shifting" synthesizer. The purpose of frequency synthesizer 86 is to shift the frequency of reference and target signals to be processed into a frequency range that is not attenuated by electronic interconnections of the circuitry and is suitable for processing by a two-phase lock-in amplifier (I-Q demodulator) 92.

First describing what may be termed a "frequency-shifting and reference-generating" branch of the electronic circuitry, at position A (the output of mixer or reference receiver 68), the frequency will be simply $f_0$, i.e., the difference or offset between the frequencies of THz-lasers 12 and 14. For purposes of this description an offset value of 2 MHz is considered. This 2 MHz frequency is input to a mixer 88 together with an input frequency $f_S$ from frequency synthesizer 86 via a splitter 90. A value of $f_S$ of 16 MHz is considered for purposes of this description. At position B (the output of mixer 88), there are frequencies $f_S \pm f_0$ (18 MHz and 14 MHz in terms of the values considered) together with residual portions of the frequency-shifting synthesizer frequency and the offset frequency, respectively $f_S$ and $f_0$ (e.g, 16 MHz and 2 MHz). Of these four frequencies output by mixer 88, only one of the shifted or mixing product frequencies (18 MHz and 14 MHz) is required. Here, the 18 MHz frequency ($f_S+f_0$) is selected by passing the output of mixer 88 through a bandpass filter 96, centered at the 18 MHz frequency and having a bandwidth of about 400 KHz at the 3 dB level. The 18 MHz output of the bandpass filter is passed to lock-in amplifier 92.

Next it is important to consider the frequency content at the output of receiver 50, for example, at position C in FIG. 2. For convenience of description, only first order sidebands and one frequency value of f(t) are considered. In this example, an instant value of 12 MHz is considered for f(t). Given this consideration, frequencies present at position C include 2 MHz and 12 GHz, being respectively the offset frequency ($f_0$) and the GHz frequency-synthesizer (synthesizer 76) frequency f(t); 12 GHz+2 MHz and 12 GHz−2 MHz, being respectively f(t)+$f_0$ and f(t)−$f_0$, i.e., the upper and lower sidebands of the frequency-modulated THz signal beam; and 24 GHz being twice the instant synthesizer frequency. It is necessary to select either the upper or lower sideband to provide a signal representative of the target to lock-in amplifier 92.

One step in this sideband selection process is to mix the sample of the output of GHz frequency synthesizer 76 with a sample of the output of frequency shifting synthesizer 86. This is accomplished by mixer 84, here, termed the SSB mixer. At the output of this mixer (position D in FIG. 2), there will be a frequency 12 GHz+16 MHz (f(t)+$f_S$), neglecting another frequency that is attenuated by at least 28 dB as a result of image rejection by the SSB mixer. The SSB mixer becomes in effect the "real" local oscillator for the apparatus. The 12 GHz+16 MHz output of the SSB mixer is heterodyned by a mixer 94 with output of receiver 50.

In considering the mixing (heterodyning) by mixer 94, it is important to note that the 2 MHz component of the output of receiver 50 will be attenuated by electronic interconnections before reaching mixer 94 and can be ignored. This being the case, the first order frequency content of the output of the output of mixer 94 (at position E in FIG. 2) will include frequencies 14 MHz, 16 MHz, 18 MHz, 24 GHz+14 MHz, 24 GHz+18 MHz, 12 GHz+16 MHz, and 36 GHz+16 MHz. The 18 MHz and 14 MHz frequencies ($f_S+f_0$ and $f_S-f_0$) are, here, respectively, the upper and lower sidebands of beam 24TR, down-mixed by the mixing processes described above, i.e., with the $v_0$ component and the 12 GHz (f(t)) component removed.

Lock-in amplifier 92 is locked to the upper sideband as a result of the 18 MHz signal input to the amplifier from bandpass filter 96 and accordingly tracks the 18 MHz signal input to the amplifier from mixer 94. It can be seen than that because the f(t) component is down mixed out of the upper sideband signal presented to the amplifier, this signal will always have the same frequency as f(t) is chirped through a selected tuning range. The phase and amplitude of the upper sideband (and lower sideband) signal will, of course, be dependent on the instantaneous vale of f(t), which is an object of the chirping, for providing range resolution, as discussed above. The lock-in amplifier will track any laser-frequency jitter since this is incidentally tracked at reference mixer 68. Phase and amplitude data in the signal provided to the lock-amplifier are processed together with X-Y position data to form, on a display 58, an image 56 of person 26 being scanned.

It should be noted that the mixer 68 of FIG. 2 combines the output of both the oscillator 12 and the oscillator 14. Since the light from the oscillator 12 reaches the mixer directly (without being scanned over the target), mixer 68 acts as a reference mixer. The output of mixer 68 can be used to track any changes in the intermediate frequency due to jitter. Since this output is delivered to the lock-in amplifier 92, it can effectively lock to this beat frequency. In the illustrated embodiment, the beat frequency is mixed down to a frequency that can be processed by the high-speed lock-in, and offset due to the input from the synthesizer 86 to enable the single-sideband reception.

The performance of the embodiment illustrated in FIG. 1 is preferably enhanced by using an IF tracking approach. To achieve this result, an additional mixer would be added identical to the mixer 68 of FIG. 2. This mixer would directly receive the output from the transmitter and the oscillator to generate a tracking signal corresponding to the intermediate (difference) frequency. The output of that mixer can then become the reference input to a lock-in (not shown in FIG. 1), or if the IF is too high for the lock-in, it can be mixed down and then used as the reference input to the lock-in. If this is done, then the lock-in will serve as a tracking IQ demodulator.

It should be noted here that while exemplary frequencies for THz-lasers 12 and 14 in the above example of the inventive apparatus have a difference of a few MHz, which would be the case if both lasers had the same gain-medium, the apparatus can include lasers having different gain-media with $f_O$ having a value in the GHz range. By way of example THz-laser 12 may be a $CH_3OH$ laser having an output frequency ($v_O$) of 2.522 THz (about 118.8 μm wavelength) and THz-laser 14 may be a $CH_2F_2$ laser having an output frequency ($v_1$) of 2.546 THz (about 117.7 μm wavelength). This would provide an offset frequency $f_0$ ($v_1-v_0$) of 24 GHz.

In an example of apparatus 60 wherein $f_0$ is 24 GHz and lock-in amplifier (I-Q demodulator) 92 is responsive in the MHz range, say to 18 MHz as described above, frequency-shifting frequency synthesizer 86 would be a GHz frequency synthesizer providing an output frequency $f_S$ of either 24 GHz+18 MHz or 24 GHz−18 MHz. Above-discussed COMSTRON GHz-frequency synthesizers have a resolution of about 500 KHz and a frequency stability of about $5\times10^{-8}$. Alternatively premixing could be carried out before mixer to bring frequencies into the MHz range, mixer 84 could operate with all inputs in the GHz range.

An advantage of providing an $f_0$ in the GHz range is that a higher data gathering rate is possible than with an $f_0$ in the MHz range. This is due to both a higher system bandwidth achievable with a higher IF, and the fact that Schottky-diode THz receivers have significantly (~30 dB) more sensitivity for IF's above 1 GHz than for an IF of 1 MHz. This is caused by the output noise characteristics of the device. Other THz receiver type benefit similarly from the higher IF frequency. It should be noted, however, that for certain liquid helium-cooled receiver types, for example, hot-electron indium antimonide (InSb) receivers, the best performance is achieved at IFs in the range of 1 MHz. For such a receiver, a preferred operation scheme would be that of apparatus 10 operating with an IF in the MHz range.

The method of the present invention is described above with reference to generating a two-dimensional (X-Y) image of concealed objects on a person. Those skilled in the art will recognize, however, without further illustration that above described embodiments of the invention could be modified to provide image data that could be used to a three-dimensional representation of the concealed objects. One such modification would be to radially scan antenna 46 and scanner 42 about an axis through the scanner to provide a number of images of the person from different angles. Those images could then be processed using well known computer tomographic methods to provide the three-dimensional representation. Alternatively, apparatus could include two scanners with antennas 46 thereof directed at different angles toward scanning region 51 to provide two two-dimensional images that could be processed and presented to provide a "stereoscopic" image.

The present invention is described above in terms of a preferred and other embodiments. The invention is not limited, however, to the embodiments described and depicted. Rather, the invention is limited only by the claims appended hereto.

What is claimed is:

1. A method of detecting objects or substances concealed in or under a person's clothing comprising:
    scanning a first beam of THz-frequency radiation, said first beam having a frequency tunable over a predetermined range, from a first source thereof;
    modulating the frequency of said first beam through said predetermined range to create a modulated frequency chirp while scanning said first beam of THz-frequency radiation over the person whereby a portion of said first beam penetrates the person's clothing and is reflected by an object or substance concealed under the person's clothing;
    mixing the reflected portion of said first beam with THz-frequency radiation from a second source thereof wherein the frequency of the radiation from the second source is different from the frequency of the first source to provide a signal having an intermediate frequency (IF) including said frequency chirp;
    demodulating the intermediate frequency as a function of the frequency chirp and deriving phase and amplitude changes induced by the interaction of the beam with the person's clothing and any object or substance concealed under the clothing;
    processing the phase and amplitude changes to produce image data representative of the concealed object or substance said image data including both intensity and range information, said range information corresponding to individual scattering sites along the propagation axis of the first beam and associated with the object or substance concealed under the person's clothing.

2. The method of claim 1, wherein said THz-frequency radiation from said second source thereof has an essentially fixed frequency.

3. The method of claim 2, wherein said predetermined range of the frequency of the THz-frequency radiation from said first source is between about 1 and 30 GHz.

4. The method of claim 1, wherein said image data is electronically processed to form a displayable image, said first beam of THz-frequency radiation is scanned over a region to be imaged, including the person, in a scan period, and wherein the period of modulation of said first-source THz-frequency is equal to said scan period divided by a number equal to the number of image elements in the displayable image.

5. The method of claim 1, wherein the beam of THz-frequency radiation is CW.

* * * * *